(12) United States Patent
Von Weymarn-Schärli

(10) Patent No.: US 8,562,517 B2
(45) Date of Patent: Oct. 22, 2013

(54) MEDICO-TECHNICAL DEVICE FOR AT LEAST PARTIALLY INTRODUCING INTO A BODY PASSAGE

(76) Inventor: Alexander Von Weymarn-Schärli, Basel (CH)

(*) Notice: Subject to any disclaimer, the term of this patent is extended or adjusted under 35 U.S.C. 154(b) by 1122 days.

(21) Appl. No.: 11/990,044

(22) PCT Filed: Aug. 8, 2006

(86) PCT No.: PCT/CH2006/000414
§ 371 (c)(1),
(2), (4) Date: Feb. 5, 2008

(87) PCT Pub. No.: WO2007/022650
PCT Pub. Date: Mar. 1, 2007

(65) Prior Publication Data
US 2010/0168716 A1    Jul. 1, 2010

(30) Foreign Application Priority Data
Aug. 26, 2005  (CH) .......................... 140/05

(51) Int. Cl.
*A61B 1/307*    (2006.01)
(52) U.S. Cl.
USPC ............... 600/139; 604/97.01; 604/103.09; 604/525; 604/524; 604/526; 604/527
(58) Field of Classification Search
USPC ............ 604/97.01, 103.09, 524–527
See application file for complete search history.

(56) References Cited

U.S. PATENT DOCUMENTS

| | | | |
|---|---|---|---|
| 4,141,364 A * | 2/1979 | Schultze | 128/207.15 |
| 5,250,069 A | 10/1993 | Nobuyoshi et al. | |
| 5,337,733 A * | 8/1994 | Bauerfeind et al. | 600/139 |
| 5,411,060 A * | 5/1995 | Chandler | 138/98 |
| 5,868,708 A * | 2/1999 | Hart et al. | 604/104 |
| 6,159,195 A | 12/2000 | Ha et al. | |

(Continued)

FOREIGN PATENT DOCUMENTS

| | | | |
|---|---|---|---|
| DE | 4406656 A1 * | 9/1995 | |
| EP | 0 371 486 A1 | 6/1990 | |
| WO | WO 2004/035124 A1 | 4/2004 | |
| WO | WO 2005/042078 A1 | 5/2005 | |

*Primary Examiner* — Nicholas Lucchesi
*Assistant Examiner* — Scott Medway
(74) *Attorney, Agent, or Firm* — Adams & Wilks

(57) ABSTRACT

The invention relates to a medico-technical device for at least partially introducing into a body passage. Said device comprises an elongate, tubular, flexible internal body (2), an elongate exterior enveloping body (3) which surrounds, at least partially, said internal body (2) on the periphery thereof, and a device (4) for transferring the device (1) from a flexible state to a rigid state and vice-versa. The invention is characterized in that the internal body (2), which is in the form of a double tube (5), comprises an inner tube (6) which forms an inner wall (8) of the internal body (2) and an external tube (7) which forms an external wall (9) of the internal body (2), said external tube (7) surrounding the inner tube (6) in a concentric manner on the periphery thereof. The invention is characterized in that the device (4) for transferring the device (1) from a flexible state into a rigid state and vice-versa is embodied in such a manner that the external tube (7) lengthens in a radial manner by increasing the pressure in an annular shaped intermediate chamber (10) and exerts pressure on the enveloping body (3).

13 Claims, 1 Drawing Sheet

(56) References Cited

U.S. PATENT DOCUMENTS

| | | | |
|---|---|---|---|
| 6,261,260 B1 * | 7/2001 | Maki et al. | 604/103.07 |
| 7,052,507 B2 * | 5/2006 | Wakuda et al. | 606/194 |
| 2004/0143239 A1 | 7/2004 | Zhou et al. | |

\* cited by examiner

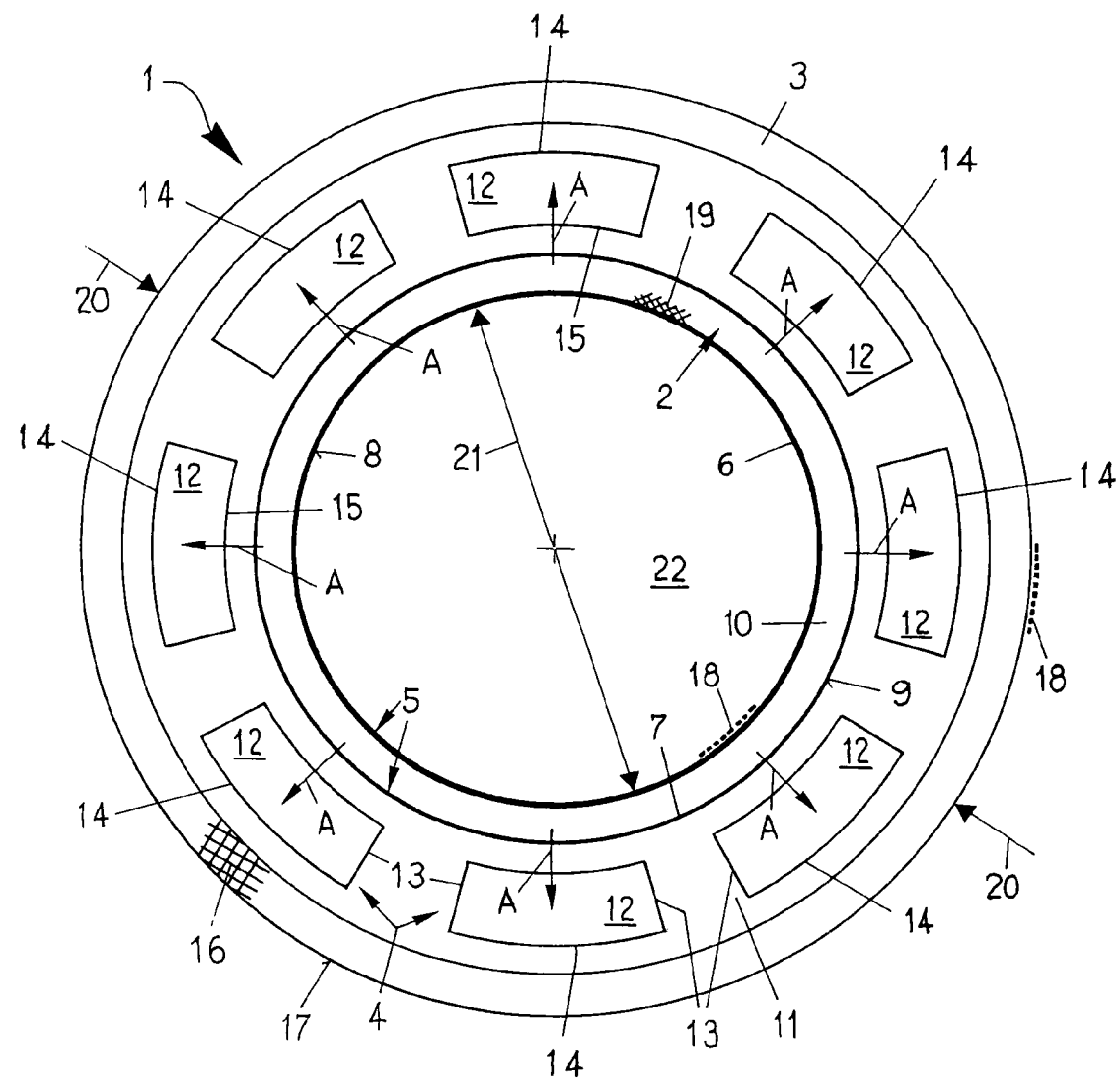

MEDICO-TECHNICAL DEVICE FOR AT LEAST PARTIALLY INTRODUCING INTO A BODY PASSAGE

CROSS-REFERENCE TO RELATED APPLICATIONS

This application is a U.S. national stage application of International Application No. PCT/CH2006/000414, filed Aug. 8, 2006, claiming a priority date of Aug. 26, 2005, and published in a non-English language.

The invention relates to a medico-technical device for introducing, at least partially, into a body passage according to the main concept of patent claim 1.

From WO 2005/042078 A1 a device is known, especially an introducer tube or a catheter, for introducing at least partially into a body passage, in which the inner body and outer envelope body each have a polygonal cross-section configured so as to allow the enveloping body and inner body to be rotatable relative to each other by a control mechanism, so that the inner body, at least partly, fits in place in the enveloping body.

A device of the type just described is known for example from WO 2004/035124 A. The known device is a guide mechanism especially for positioning catheters in a body passage. It has a tube-like inner body, which is configured as the first thread. This is made of an extensible, elastic material and closely enveloped round its periphery by several second threads made of wire leaving interstitial gaps. The inner body called the first thread can, when in its extended state, exert a radially acting pressure on the several second threads. For this the interior of the inner body can be filled out using a pressurized fluid, preferably a liquid. The disadvantage here is that the known device can only be used solely as a so-called guide mechanism for positioning catheters.

The invention has the purpose of producing a medico-technical device of the type described at the start which is more versatile and has a better handling.

This objective is solved according to the invention by a medico-technical device with the characteristics of patent Claim 1.

In the invention the internal body in the form of a double tube comprises an inner tube which forms the inner wall of the internal body and an outer tube, concentrically surrounding the periphery of the inner tube, which forms an outer wall of the inner body; and here the mechanism to transfer the device from a flexible to a rigid state and vice versa is formed by the outer tube being caused to expand radially by increasing the pressure in an annular shaped intermediate chamber of the inner body and by this means directly, or indirectly by further means, exerting a pressure on the enveloping body. This makes it possible for the inner body to have an interior whose size can be specified. Thus for example the inner diameter of the inner body can be at least 1 to 5 or more mm and therefore serve to receive, for example, a catheter. The medico-technical inventive device can therefore be either a so-called guide mechanism especially for positioning of catheters in a body passage, or it can also even be a mechanism for introducing into a body passage, at least partially, in particular an introducer tube or a catheter. Thus a defined space in the inner body is available, where thanks to the extensibility of the outer tube of the inner body there is nonetheless the possibility of transferring the entire mechanism from a mainly flexible state to a mainly rigid state, which may also be curved just as needed, and vice versa.

It is advantageous to have the outer tube made of a material which is more extensible than that of the inner tube, preferably by the thickness of the outer tube being less than that of the inner tube. By this means one ensures that an increase of the pressure in an annular intermediate chamber between inner tube and outer tube leads almost exclusively to an expansion of the outer tube, and not for example a shrinking of the inner tube, so that the latter can retain its inner measurement almost unchanged. By reducing the thickness of the material of the outer tube as compared to that of the inner tube it is possible in a specially simple and economic way to configure the outer tube to be more extensible and therefore more elastic than the inner tube.

According to another further development of the invention, several bands preferably of metal are set out in an annular intermediate chamber between the inner body and the enveloping body, extending in the longitudinal direction of the device and preferably equidistant from each other, where the bands can preferably be pressed against the enveloping body by a radial extension of the outer tube. On the one hand the longitudinal bands enable a great flexibility, i.e. bendability, of the inventive device, on the other hand they can also help to enable the entire device to be made largely resistant to bending. Furthermore the bands can also help to ensure an advantageous, primary rigidity of the device, so that it can be more easily pushed into a body passage or also into a branch of a body passage. As completely flexible devices are less suitable for pushing into a body passage than those with a certain prior rigidity. The prior rigidity could also be termed initial rigidity. In this way the usefulness and the handling of the inventive device are effectively improved.

According to an advantageous further development of the invention, the enveloping body is configured to be flexibly bendable, while yet resistant to torsion, and preferably it has a net and/or a fabric and/or at least two coils running in opposite directions. By this means the flexible handling of the inventive device is further improved. The configuration of this device is therefore especially rigid against twisting. This is all the more so because not only, as mentioned before, the bands, but also the enveloping body improve the torsional strength of the device.

It is advantageous if the inner body, at least on the inside of its inner tube, and/or the enveloping body at least on its outside, has a hydrophilic coating. By this means an advantageously thin film of water remains on the inside and/or outside of the device, which allows an optimising of the lubrication for example in a catheter or in a vessel such as a body passage. By this means, too, it is possible to further improve the versatility and handling of the inventive device.

According to another further development of the invention, the inner body is stiffened by a wire and/or a mesh around the periphery, where preferably the wire and/or the mesh are made of steel or a titanium-nickel alloy, preferably Nitinol®. By this means the inner body can, for example, be further stabilised, whereby the wire may, for example, be run through the inner body like a core and advantageously can contribute to a certain primary rigidity of the inner body and therefore of the whole device. Nitinol® is a material with a certain "memory capacity", which is temperature dependant. This material is for example used for stents. At normal ambient temperatures this material is usually soft. At a raised temperature it can become hard.

According to another further development of the invention, the outer diameter of the device tapers and gets smaller towards its front end, preferably smoothly. By this means the versatility or handling of the inventive device can be further improved, since in this way it may be possible to reach narrow or hard-to-reach vessels or body passages, or branches of such vessels and body passages, with the device.

Examples of embodiments of the object of invention will now be explained in more detail, referring to the drawing; here all the features which are described and/or which are represented in the image form by themselves or in any desired combination the object of the present invention, independent of their summary in the claims or the related references therein, the sole FIGURE showing:

a schematic cross-section through a medical device for introducing at least partially into a body passage.

In FIG. 1 is schematically shown a cross-section through a medico-technical device 1 for introducing at least partially into a not specifically depicted body passage.

The medico-technical device 1, hereinafter referred to in brief as the device, has a longitudinal, tube-shaped, flexible internal body 2 as well as a longitudinal outer enveloping body 3 surrounding at least some sections of its periphery. For better clarity the hatching to signify a cut-out has been omitted in the sole FIGURE.

Moreover the device 1 has a mechanism 4 for transferring the device from a flexible to a rigid and, as needed, curved state and vice versa.

According to the invention the internal body 2 is configured in the form of a double tube 5 with an inner tube 6 and an outer tube 7. The inner tube 6 forms an inner wall 8 of the internal body 2, the outer tube 7 forms an outer wall 9 of the internal body 2, with the outer tube 7 surrounding the periphery of the inner tube 6 more or less concentrically.

In the embodiment example shown in the FIGURE, the mechanism 4 for transferring the device 1 from a flexible to a rigid state and vice versa is formed by the outer tube 7 being made to expand radially in the direction of the arrows A by increasing the pressure in an annular intermediate chamber 10, and thereby exerting a pressure on the enveloping body 3.

According to a preferred embodiment of the invention the outer tube 7 is made of a material which is more extensible than that of the inner tube 6. This increased extensibility of the material of the outer tube 7 can for example be achieved by making the thickness of the outer tube 7 less than that of the inner tube 6.

As shown in the FIGURE, several bands 12, preferably equidistantly separated from each other, are arranged in an annular intermediate chamber 11 between the longitudinal bands and then on the periphery of the internal body 2 and enveloping body 3. The bands 12 primarily extend in the longitudinal direction of the device 1 and are preferably made of metal. By the radial extension of the outer tube 7 in the direction of the arrows A, the bands 12 can be pressed against the enveloping body 3, by which means the rigidity of the entire device 1 is increased, also while in a curved state. The radial extension of the outer tube 7 can be produced by introducing a pressurized fluid, such as a liquid or a gas, into the annular intermediate chamber 10 of the internal body 2.

The bands 12 may have a small distance between them. The edges 13 of the bands facing each other may run parallel to each other or preferably converge at a conical angle towards the inside. Also the outside edges 14 of the bands 12 may be curved and their radius matched to that of the enveloping body 3 or they may run straight. Analogous embodiments also apply for the inner edges 15 of the bands 12.

According to a specially preferred embodiment of the invention the enveloping body 3 is configured as flexibly bendable, yet torsion-resistant. For this the enveloping body 3 has a net 16 and/or a fabric and/or at least two spiral coils running in opposite directions, not shown in detail. The enveloping body 3 may itself be configured as a kind of net or have such a mesh or a fabric inside it. In the FIGURE the structure of the mesh 16 is merely indicated schematically at one point.

According to another embodiment of the invention the internal body 2 at least on the inner wall 8 of its inner tube 6 and/or the enveloping body 3 at least on its outside 17, has a hydrophilic coating 18, which in the FIGURE is again merely indicated schematically at one point. Similarly the hydrophilic coating 18 on the inner wall 8 of the inner tube 6 is merely shown schematically.

According to a further preferred embodiment of the invention, the internal body 2 is stiffened by means of a wire and/or a mesh 19 around the periphery. This stiffening may, as indicated schematically in the FIGURE, be arranged in the annular intermediate chamber 10 of the internal body 2. It is also possible, however, to provide the mesh on the inner wall 6 and/or on the outer wall 9 of the internal body 2.

The wire which is not specifically shown and/or the mesh 19 are preferably made of steel or a titanium-nickel alloy, preferably of Nitinol®.

According to another, not specifically shown embodiment of the invention the outside diameter 20 of the device 1 tapers down towards its front end, preferably in a smooth gradation.

The device 1 can thus be applied both as introducer tube or catheter and yet also as a so-called guide mechanism for a catheter, whereby in the latter case the inner diameter 21 of the internal body 2 is at least 1 to 5 or more mm. In the latter embodiment a catheter could thus be pushed through the interior 22 of the internal body 2. Alternatively the inventive device could also be used as a so-called guide mechanism, by for example pushing a catheter over the device. Clearly in both cases the dimensions in the FIGURE are shown greatly enlarged.

Now the application of the medico-technical inventive device will be explained using examples.

Usually the device 1 is inserted into a body passage, such as an artery or a vein, while in the unstiffened state, and pushed through in the body passage up to the desired location to be examined. Here the device has a certain primary or basic rigidity, which is made possible for example by the bands 12, the net 16 or the mesh 19.

When the device is to be transferred with the aid of the mechanism for transferring the device from a flexible to a rigidified state, a pressure is applied to the double tube 5 for example by means of a pressurised medium, such as a liquid or a gas. This pressure causes an increase in the outer diameter of the double tube 5, as the outer tube 7 moves outward following the radially directed arrows A. Here the inner diameter 22 of the internal body 2 remains entirely or to a large extent as it was. If present, the said bands 12 can finally be pressed against the enveloping body 3 with the aid of the outer tube 7 as it moves radially outward. Thus the radial expansion of the outer tube 7 of the internal body 2 contributes to a stiffening of the entire medico-technical device 1.

The inventive device can, as previously mentioned, be applied both as introducer tube or catheter and as guide mechanism.

The curvature or radius of the outer edge 14 of each band 12 may be matched to the radius or curvature of the enveloping body 3. Moreover the inner edge 15 of these bands may be matched to the outside diameter of the internal body 2 and correspond to the latter. This applies both for the flexible and the rigidified state of the device described.

In this manner a medico-technical device is produced which can be used in a greater variety of ways and is better in its handling.

The invention claimed is:

1. A device for introduction into a body passage, comprising: an elongate, flexible tubular inner body having an inner tube and an outer tube that surrounds the inner tube and that is radially spaced from the inner tube to define therebetween a first annular chamber which receives a pressurized fluid for extending the outer tube radially outwardly; an elongate, flexible tubular enveloping body that surrounds and envelops the tubular inner body at least partially along the length of the tubular inner body and that is radially spaced from the tubular inner body to define therebetween a second annular chamber; and a plurality of stiffening bands for transferring the device from a flexible state to a rigid state and vice versa, the stiffening bands being disposed in the second annular chamber and extending lengthwise along the second annular chamber in circumferentially spaced-apart relation to one another and being pressed against the tubular enveloping body by radial outward extension of the outer tube to place the device in its rigid state.

2. A device according to claim 1; wherein the outer faces of the stiffening bands are curved with a curvature that matches the curvature of the tubular enveloping body.

3. A device according to claim 1; wherein the outer tube is made of a material that is more extensible than that of the inner tube.

4. A device according to claim 1; wherein the thickness of the outer tube is less than that of the inner tube.

5. A device according to claim 1; wherein the tubular enveloping body is flexibly bendable but resistant to torsion.

6. A device according to claim 5; wherein the tubular enveloping body includes a net, fabric or mesh to increase the torsional resistance thereof.

7. A device according to claim 1; wherein the tubular inner body is stiffened by a wire or mesh around its periphery.

8. A device according to claim 1; wherein the inner faces of the stiffening bands are curved with a curvature that matches the curvature of the outer tube of the tubular inner body.

9. A device according to claim 8; wherein the stiffening bands have opposed side faces that taper inwardly from the outer faces to the inner faces.

10. A device according to claim 1; including a hydrophilic coating on the inside surface of the inner tube or on the outside surface of the tubular enveloping body, or on both the inside and outside surfaces.

11. A device according to claim 1; wherein the inner tube has an inner diameter large enough to permit a catheter to be axially inserted therethrough.

12. A device according to claim 1; wherein the inner tube has an inner diameter 1 to 5 mm.

13. A device according to claim 1; wherein the inner tube has an inner diameter greater than 5 mm.

* * * * *